United States Patent [19]

McNamara et al.

[11] Patent Number: 4,681,873

[45] Date of Patent: Jul. 21, 1987

[54] 4-AMINO-3-HALO-2-PYRIDINONE NUCLEOSIDE AND NUCLEOTIDE COMPOUNDS

[75] Inventors: Dennis J. McNamara; Phillip D. Cook, both of Ann Arbor, Mich.

[73] Assignee: Warner-Lambert Company, Morris Plains, N.J.

[21] Appl. No.: 759,816

[22] Filed: Jul. 29, 1985

[51] Int. Cl.$^4$ .................. A61K 31/70; C07H 17/00
[52] U.S. Cl. .................................. 514/50; 514/51; 536/23; 536/29
[58] Field of Search ............... 536/23, 29; 514/50, 514/51

[56] References Cited

U.S. PATENT DOCUMENTS

| | | | |
|---|---|---|---|
| 2,802,005 | 8/1957 | Heidelberger et al. | 544/313 |
| 2,885,396 | 5/1959 | Heidelberger et al. | 536/23 |
| 3,201,389 | 8/1965 | Fujimoto et al. | 536/29 |
| 3,317,542 | 5/1964 | Haszeldine et al. | 546/296 |
| 3,355,278 | 10/1967 | Well et al. | 71/94 |
| 3,853,897 | 12/1974 | Witzel et al. | 546/297 |
| 4,526,988 | 7/1985 | Hertel | 536/23 |

FOREIGN PATENT DOCUMENTS

| | | |
|---|---|---|
| 0724667 | 12/1967 | Belgium . |
| 0758758 | 5/1971 | Belgium . |
| 758759 | 5/1971 | Belgium . |
| 209222 | 6/1981 | Japan . |
| 2136425 | 3/1984 | United Kingdom . |

OTHER PUBLICATIONS

Nesnow et al, J. Het. Chem. 12(5): 941–944, 1975.

Primary Examiner—Johnnie R. Brown
Assistant Examiner—John W. Rollers, Jr.
Attorney, Agent, or Firm—Jerry F. Janssen

[57] ABSTRACT

4-Amino-3-halo-1-β-D-ribofuranosyl-2-(1H)-pyridinone, 4-amino-3-halo-1-(2-deoxy-β-D-pentofuranosyl)-2(1H)-pyridinone, and nucleosides and 4-amino-3-halo-1-(2-deoxy-2,2-difluoroβ-D-pentofuranosyl)-2(1H)-pyridinone nucleosides and nucleotides are useful as antiviral agents and possess in vivo activity against the L1210 murine leukemia cell line.

20 Claims, No Drawings 4,681,873

4-AMINO-3-HALO-2-PYRIDINONE NUCLEOSIDE AND NUCLEOTIDE COMPOUNDS

BACKGROUND OF THE INVENTION

The present invention relates to chemical compounds, pharmaceutical compositions, and methods of preparing and using the compounds. More particularly, it is concerned with certain 4-amino-3-halo-2-pyridinone nucleosides and nucleotides, with pharmaceutical compositions containing these compounds, and with methods for preparing the compounds, and for their pharmaceutical use.

SUMMARY OF THE INVENTION

In one aspect, the present invention provides compounds having the structural formula 1

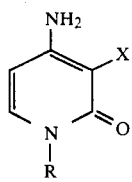

where R is selected from

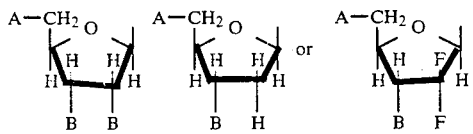

wherein X is chlorine, fluorine, or bromine, A is hydrogen, —OPO₃H₂, benzoyl, 4-methylbenzoyl, or straight or branched alkanoyl of from one to six carbons, and B is hydrogen, benzoyl, 4-methylbenzoyl, or straight branched alkanoyl of from one to six carbon atoms, and the pharmaceutically acceptable salts thereof.

In another aspect, the present invention provides a method of preparing compounds of formula 1 above which comprises reacting a 4-amino-3-halo-2(1H)-pyridinone of formula 2

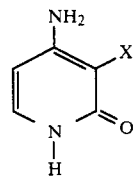

where X is fluorine, chlorine, or bromine, with a compound of formula 3

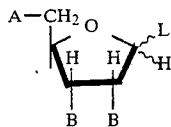

where L is a leaving group selected from acetyl, chloro, bromo, or methanesulfonyl, and A and B are protecting groups selected from benzoyl, 4-methylbenzoyl or alkanoyl of from one to six carbon atoms, thereafter if desired, removing said protecting groups to produce the compound where A and B are hydrogen and further, if desired, reacting the compound where A and B are hydrogen with phosphoryl chloride to form the compound where A is —OPO₃H₂ and B is hydrogen.

In yet another aspect, the present invention provides a method of preparing compounds of formula 1 above which comprises reacting a 4-amino-3-halo-2(1H)-pyridinone of formula 2

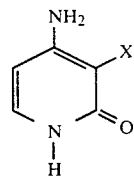

where X is fluorine, chlorine, or bromine, with a compound of formula 4

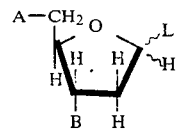

where L is a leaving group selected from acetyl, chloro, bromo, or methanesulfonyl, A and B are protecting groups selected from benzoyl, 4-methylbenzoyl or alkanoyl of from one to six carbon atoms thereafter if desired, removing said protecting groups to produce the compound where A and B are hydrogen and further, if desired, reacting the compound where A and B are hydrogen with phosphoryl chloride to form the compound where A is —OPO₃H₂ and B is hydrogen.

In another aspect, the present invention provides a method of preparing compounds of formula 1 above which comprises reacting a 4-amino-3-halo-2(1H)-pyridinone of formula 2

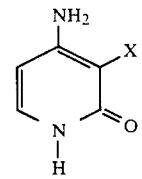

where X is fluorine, chlorine, or bromine, with a compound of formula 5

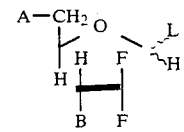

where L is a leaving group selected from acetyl, chloro, bromo, or methanesulfonyl, A and B are protecting groups selected from benzoyl, 4-methylbenzoyl or alkanoyl of from one to six carbon atoms thereafter if desired, removing said protecting groups to produce the compound where A abd B are hydrogen and further, if desired, reacting the compound where A and B are hydrogen with phosphoryl chloride to form the compound where A is —OPO₃H₂ and B is hydrogen.

In yet another aspect, the present invention also provides pharmaceutical compositions for inhibiting virus growth comprising an virus growth inhibiting amount of a compound of formula 1 in combination with a pharmaceutically acceptable carrier.

In another aspect, the present invention provides a method of treating viral infections in a mammal which comprises administering to a mammal in need of such treatment an antivirally effective amount of a compound having structural formula 1 in combination with a pharmaceutically acceptable carrier.

DETAILED DESCRIPTION

The present invention provides a class of 4-amino-3-halo-2(1H)-pyridinone nucleoside and nucleotide compounds which are useful as antiviral agents and which additionally demonstrate in vivo activity against the L1210 murine leukemia cell line.

The compounds of the present invention possess a chemical structure in which an aglycone selected from the group 4-amino-3-fluoro-2(1H)-pyridinone, 4-amino-3-chloro-2(1H)-pyridinone, and 4-amino-3-bromo-2(1H)-pyridinone is coupled through the ring nitrogen atom to a pentose selected from $\beta$-D-ribofuranose, or the 2-deoxypentoses 2-deoxy-$\beta$-D-ribofuranose, or 2-deoxy-2,2-difluoro-$\beta$-D-ribofuranose. The pentose or deoxypentose portion of the compounds may also be O-substituted with straight or branch-chained alkanoyl groups of from one to six carbon atoms, benozyl, 4-methylbenzoyl, or may be O-phosphorylated at the 5-hydroxy position. Preferred compound of the present invention include those where (a) the glycone hydroxyl functions are all unsubstituted, (b) the 5-hydroxy group of the aglycone is phosphorylated, or (c) all of the glycone hydroxyl groups are similarly substituted with benzoyl, 4-methylbenzoyl, or acyl of from one to six carbon atoms.

In one preferred embodiment, compounds of the present invention are those of structural formula 1 above where R is

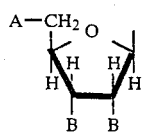

and where A and B are as previously defined.

In another preferred embodiment, compounds of the present invention are those of structural formula 1 above where R is

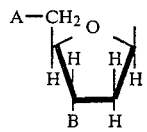

and where A and B are as previously defined.

In yet another preferred embodiment, compounds of the present invention are those of structural formula 1 above where R is

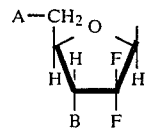

and where A and B are as previously defined.

Particularly preferred compounds of the present invention are those having the names:
4-Amino-3-fluoro-1-$\beta$-D-ribofuranosyl-2(1H)-pyridinone;
4-Amino-3-fluoro-1-(5-O-phosphono-$\beta$-D-ribofuranosyl)-2(1H)-pyridinone;
4-Amino-3-fluoro-1-(5-O-phosphono-$\beta$-D-ribofuranosyl)-2(1H)-pyridinone, disodium salt;
4-Amino-3-fluoro-1-(2,3,5-tri-O-acetyl-$\beta$-D-ribofuranosyl)-2(1H)-pyridinone;
4-Amino-3-fluoro-1-(2,3,5-tri-O-benzoyl-$\beta$-D-ribofuranosyl)-2-(1H)-pyridinone;
4-Amino-1-(2-deoxy-$\beta$-D-erythro-pentofuranosyl)-3-fluoro-2(1H)-pyridinone;
4-amino-1-(2-deoxy-5-O-phosphono-$\beta$-D-erythro-pentofuranosyl)-3-fluoro-2(1H)-pyridinone;
4-amino-1-(2-deoxy-5-O-phosphono-$\beta$-D-erythro-pentofuranosyl)-3-fluoro-2(1H)-pyridinone, disodium salt;
4-amino-1-(2-deoxy-3,5-di-O-acetyl-$\beta$-D-erythropentofuranosyl)-3-fluoro-2(1H)-pyridinone;
4-amino-1-[2-deoxy-3,5-di-O-(4-methylbenzoyl)-$\beta$-D-erythro-pentofuranosyl]-3-fluoro-2(1H)-pyridinone;
4-Amino-3-bromo-1-(2,3,5-tri-O-benzoyl-$\beta$-D-ribofuranosyl)-2(1H)-pyridinone;
4-Amino-3-bromo-1-($\beta$-D-ribofuranosyl)-2(1H)-pyridinone;
4-Amino-3-chloro-1-(2,3,5-tri-O-benzoyl-$\beta$-D-ribofuranosyl)-2(1H)-pyridinone; and
4-Amino-3-chloro-1-($\beta$-D-ribofuranosyl)-2(1H)-pyridinone.

The starting materials 3-bromo- and 3-chloro-4-amino-2(1H)-pyridinone are prepared by reacting 4-amino-2(1H)-pyridinone, (Cook, et al., *J. Het. Chem.*, 14: 1295, 1977), with N-bromo- or N-chlorosuccinimide, respectively. The reaction is carried out in an unreactive polar solvent such as glacial acetic acid, generally at ambient temperatures. The product is purified from the crude reaction mixture by chromatographic methods.

The starting material 3-fluoro-4-amino-2(1H)-pyridinone, is prepared by the method depicted schematically in the following Reaction Sequence.

Pentafluoropyridine, 6, (Aldrich Chemical Company, Milwaukee, Wisc.) is converted to 4-amino-2,3,5,6-tetrafluoropyridine, 7, by reaction with aqueous ammonia solution in a closed vessel at temperatures between about 100° C. and 150° C. for a period of between about one to five hours.

Compound 7 is converted to 4-amino-3,5,6-trifluoro-2(1H)-pyridinone, 8, by reaction with with aqueous sodium hydroxide solution under reflux.

Reaction of 8 with hydrazine in an alcoholic solvent such as ethanol under reflux for a period of from about 4 hours to 24 hours produces 4-amino-3-fluoro-2(1H)-pyridinone, 9a, together with small amounts of the isomeric 4-amino-5-fluoro-2(1H)-pyridinone 9b.

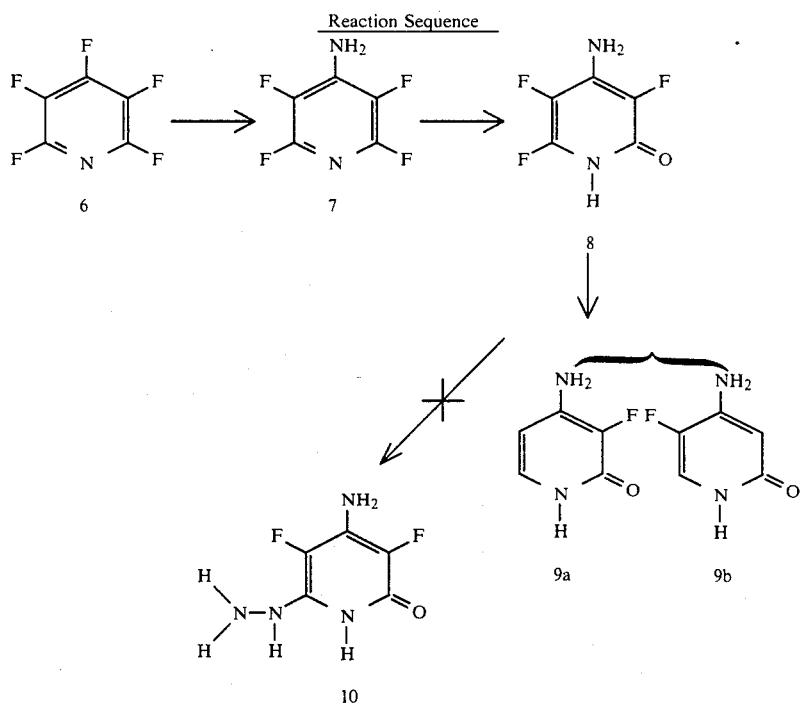

Reaction Sequence

The results of this hydrazine defluorination step are surprising since the product expected from the reaction, by analogy to known reactions of the same type, was 4-amino-3,5-difluoro-6-hydrazino-2(1H)-pyridinone 10 which would arise from the replacement of the fluorine atom at the 6-position.

The starting carbohydrate materials, including D-ribose, 1-O-acetyl-2,3,5-tri-O-benzoyl-D-ribose, D-2-deoxyribose, and 1-O-acetyl-2,3,5-tri-O-benzoyl-D-2-deoxy-ribose are commercially available materials or are synthesized from known starting materials by methods known in the art.

2-Deoxy-2,2-difluoro-D-ribose is prepared by the method detailed in United Kingdom Patent Application No. 2,136,425 A published Sept. 19, 1984.

Efficient coupling of the 4-amino-3-fluoro-, 4-amino-3-chloro-, or 4-amino-3-bromo-2(1H)-pyridinone aglycone, to the desired substituted or unsubstituted ribose 11, 2-deoxyribose 12, or 2-deoxy-2,2-difluoro-D-ribose 13, is promoted by first employing a derivative of the pentose or deoxy-pentose having an appropriate leaving group at the 1-position of the carbohydrate. Leaving groups such as acetate, methanesulfonate, chloride, or bromide may be used for this purpose, with acetate being preferred.

The 1-acetate derivatives, if not commercially available, are prepared from the corresponding 1-hydroxy compounds by reaction with acetic anhydride, acetyl chloride, or other suitable source of acetate, in the presence of an equivalent amount of an acid scavenger. The 1-O-methanesulfonate are similarly prepared by reaction of the carbohydrate with methanesulfonyl chloride. The chlorides or bromides are prepared from the corresponding 1-O-acetates by reaction with the appropriate hydrohalic acids at temperatures between about −50° C. and 0° C.

The 1-O-acetate compounds are coupled to 4-amino-3-fluoro-2(H)-pyridinone by heating the 4-amino-3-halo-2(1H)-pyridinone under reflux in hexamethyldisilazane in the presence of ammonium sulfate. The intermediates thus formed are reacted in the presence of a small amount of Lewis acid catalyst such as stannic chloride with the protected sugar moiety. This reaction is generally carried out in an inert solvent such as 1,2-dichloroethane at temperatures below about 5° C. for a period of from about 10 minutes to about on hour, followed by a further reaction period of from one to three hours at room temperature.

The reactions in which the carbohydrates are coupled to 4-amino-3-halo-2(1H)-pyridinones to form the compounds of this invention generally require that other hydroxyl groups on the carbohydrates be protected by groups which may later be easily removed, if desired. Suitable protecting groups are those commonly employed for the prupose in synthetic organic chemistry, such as those described in "Protective Groups in Organic Chemistry," McOmie, Plenum Press, London, 1973 and "Protective Groups in Organic Synthesis," Greene, John Wiley & Sons, New York, 1981.

Examples of such hydroxy-protecting groups include acetyl, chloroacetyl, methoxyacetyl, phenoxyacetyl, benzoyl, 4-methylbenzoyl, 4-nitrobenzoyl, diphenylmethyl, triphenylmethyl, ethoxycarbonyl, phenoxycarbonyl, benzyloxycarbonyl, methoxymethyl, 2-methoxyethoxymethyl, tetrahydropyranyl, allyl, and tetrahydrothienyl groups, with acyl groups of from one to six carbon atoms (particularly acetyl), benzoyl, and 4-methylbenzoyl being most preferred.

Silyl hydroxy-protecting groups may also be used in particular circumstances when other protecting groups are to be retained because they are easily cleaved by the action of reagents such as water or alcohols which do not normally cleave other protecting groups. Suitable silyl protecting groups include trimethylsilyl, as well as isopropyldimethylsilyl, methyldiisopropylsilyl, or triisopropylsilyl.

In preparing compounds of the present invention, it is preferred that the 1-O-acetyl-2,3,5-tri-O-benzoyl-D- ribose, 1-O-acetyl-3,5-di-O-benzoyl-2-deoxyribose or 1-O-acetyl-3,5-di-O-benzoyl-2,2-difluoro-2-deoxyribose be first coupled with the 4-amino-3-halo-2(1H)-pyridinone and the protecting groups at positions 2, 3, and 5 subsequently removed, if desired. This de-protection step is carried out by reacting the compound with sodium methoxide in methanol. This reaction is generally carried out at room temperature for a period of about 24 hours.

The hydroxyl functions may then be protected by other protecting groups, if desired, by conventional reactions, or the 5-position of the unprotected nucleoside may be phosphorylated, for example by reaction with phosphoryl chloride in trimethylphosphate at temperatures below about 10° C. for a period of from one to five hours.

Compounds of the present invention in which the 5-hydroxyl function of the carbohydrate moiety has been phosphorylated are capable of existing as both the free acid and as salts. Pharmaceutically acceptable salts of the phosphate moiety include, but are not necessarily limited to, the alkali and alkaline earth metals, e.g. lithium, sodium, potassium, calcium, and magnesium. Also the phosphate moiety of compounds of this invention form salts with ammonia and with pharmaceutically acceptable amines such as mono-, di-, and trialkylammonium where alkyl comprises one to four carbon atoms, octylammonium, cetyltrimethylammonium, and cetylpyridinium.

The salts are formed by upward adjustment of the pH of an aqueous or aqueous-alcoholic solution of the free acid form of the phosphate derivative with the desired base. When the desired amount of base has been added to neutralize one or both of the acidic functionalities of the phosphate moiety, the salt is recovered by evaporation of the solvent and further purification, if needed, by techniques known in the art.

The free acid form the compounds may be recovered from the base addition salts, if desired, by contacting an aqueous solution of the salt with a suitable ion exchange resin such as IRC-50 (Dow Chemical Co., Midland, Mich., USA) in the hydrogen ion form, or by careful acidification with an aqueous solution of an acid such as hydrochloric.

The compounds of the present invention may exist in the solvated or unsolvated form with water or other pharmaceutically acceptable solvents such as methanol, ethanol, and the like. The solvated forms of the compounds of this invention may differ from the unsolvated forms in such physical properties as melting point and solubility in polar solvents such as water, but the two forms are otherwise considered equivalent for the purposes of this invention.

The compounds of the present invention are useful as antiviral agents. For example, the compound 4-amino-3-fluoro-1-$\beta$-D-ribofuranosyl-2(1H)-pyridinone, in accordance with the present invention, demonstrated marked activity against the Rhino-2 and Vaccinia viral strains and slight activity against the Herpes Types I and II viral strains in the virus rating (VR) method reported by Sidwell et al., *Appl. Microbiol.*, 22: 79 (1971). VR values of 1.10 and 1.41 were obtained for this compound when tested against the Rhino-2 and Vaccinia viral strains, respectively, and VR values of 0.38 and 0.35 when tested against the Herpes Type I and Type II viral strains, respectively.

According to this test, a VR value of 1.0 or greater indicates definite antiviral activity, values between 0.5 and 1.0 indicate moderate activity, and values below 0.5 indicate marginal activity.

Further, the compounds of the present invention demonstrate in vivo activity against the transplanted L1210 leukemia cell line in mice. In this test, detailed by Geran et al., *Cancer Chemotherapy Reports*, Part 3, Vol. 3 (2): 1–87, L1210 cells harvested from the ascites fluid of leukemic male DBA$_2$ mice are diluted with sterile 0.9% saline containing 2.1% w/v bovine serum albumin and 2000 units/ml of penecillin and 0.3 mg/ml streptomycin. The cells are counted, and subject mice are randomized, and inoculated with $10^4$ L1210 cells intraperitoneally (0.5 ml). The mice are then rerandomized to control or treatment groups on Day 0.

The compound to be tested is dissolved in 10% aqueous dimethylsulfoxide and the treatment group of mice are injected intraperitoneally daily with 0.5 ml of freshly prepared solution on Days 3–7. All mice are weighed daily on days 3–7 and any non-servivors are autopsied to confirm the presence of leukemia.

The ratio of median life span of treated to control mice (expressed as a percentage) is recorded as a %T/C value. %T/C values of 125 or greater are considered indicative of marked activity against the L1210 murine leukemia cell line.

The compound 4-amino-3-fluoro-1-$\beta$-D-ribofuranosyl-2(1H)-pyridinone exhibited %T/C values of 208, 216, 185, 157, and 136 at dosages of 200, 100, 50, 25, and 12.5 mg/kg/injection. The tri-O-acetyl derivative, 4-amino-3-fluoro-1-(2,3,5-tri-O-acetyl-$\beta$-D-ribofuranosyl-2(1H)-pyridinone exhibited somewhat lower, but still marked activity having %T/C values of 186, 190, 168, 129, and 109 at dosages of 200, 100, 50, 25, and 12.5 mg/kg/injection.

When employped as pharmacological agents or pharmaceutical compositions, the compounds of the present invention are prepared and administered in any of a wide variety of topical, oral, rectal, or parenteral dosage forms.

For preparing pharmaceutical compositions, one employs an inert, pharmaceutically acceptable carrier which can be either solid or liquid. Solid form preparations include powders, tablets, dispersible granules, capsules, cachets, and suppositories. A solid carrier can also be one or more substances which also act as diluents, flavoring agents, solubilizers, lubricants, suspending agents, binders, or tablet disintegrating agents; it can also be an encapsulating material.

In powders, the carrier is a finely divided solid which is in admixture with the finely divided active compound. In tablets, the active component is mixed with carrier having the necessary binding properties in suitable proportion and compacted in the shape and size desired. The powders and tablets preferably contain from 5 to 20 percent by weight of the active component. Suitable solid carriers include magnesium carbonate, magnesium stearate, talc, sugar, lactose, pectin, dextrin, starch, gelatin, tragacanth, methyl cellulose, sodium carboxymethyl cellulose, a low-melting wax, cocoa butter, and the like.

The term "preparation" is intended to include the formulation of the active compound with an encapsulating material serving as carrier providing a capsule in which the active component (with or without additional carriers) is surrounded. Similarly, cachets are included. Tablets, powders, cachets, and capsules can be used as solid dosage forms suitable for oral administration.

Liquid form preparations include solutions, suspensions, and emulsions. A typical example of a liquid form preparation is a water or water-propylene glycol solution for parenteral administration. Liquid preparations may also be formulated in solution in aqueous polyethylene glycol. Aqueous solutions for oral administration are prepared by dissolving the active component in water and adding suitable colorants, flavoring agents, stabilizers, and thickening agents as desired. Aqueous suspensions suitable for oral use are made by dispersing the finely divided active component in water with a viscous material, for example, natural or synthetic gums, resins, methyl cellulose, sodium carboxymethyl cellulose, and other suspending agents.

Topical preparations include creams, lotions, gels, and sprays. These various topical preparations may be formulated by well-known procedures. See for example, Remington's Pharmaceutical Sciences, Chapter 43, 14th Ed., Mack Publishing Co., Easton, Pa., 18042, USA.

Preferably, the pharmaceutical preparation is in unit dosage form. In such form, the preparation is subdivided into unit doses containing appropriate quantities of the active compound. The unit dosage form can be a packaged preparation with the package containing discrete quantities of the preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active compound. A dose range of about 0.5 to about 10 mg per kilogram is preferred. Determination of the proper dosage for a particular situation is within the skill of the art.

Generally, treatment is initiated with smaller dosages which are less than the optimum dose of the compound. Thereafter the dosage is increased by small increments until the optimum effect under the circumstances is reached. For convenience, the daily dosage may be divided and administered during the day if desired.

The compound may also be administered paranterally or intraperitoneally. Solutions of the compound are prepared in water mixed, if desired, with a surfactant such as hydroxypropylcellulose. Dispersions can also be prepared in glycerol, liquid polyethylene glycols, in oils, or in mixtures thereof. These preparations may also contain preservatives and/or stabilizers to enhance the shelf-life of the preparations under ordinary conditions of storage.

Pharmaceutical preparations suitable for parenteral administration include sterile aqueous solutions or dispersions and sterile powders for use in the contemporaneous preparation of sterile injectable solutions or dispersions. The carrier can be a solvent or dispersion medium containing, for example, water, ethanol, polyol (e.g. glycerol, propylene glycol, liquid polyethylene glycol, and the like), N,N-dimethylacetamide, suitable mixtures thereof and vegetable oils.

Proper fluidity of liquid preparations can be maintained, for example, by the use of a coating material such as lecithin, by the maintenance of the required particle size in the case of dispersions, and by the use of sufactants.

Prevention of the growth of microorganisms in the preparations can be effected by the inclusion of various antibacterial or antifungal agents. For example, parabens, chlorobutanol, phenol, sorbic acid, thimerosal and the like.

The preparations may also contain agents to promote the isotonicity of the preparation with body fluids. Suitable materials for this purpose include sodium chloride and sugars such as dextrose.

Sterile injectable solutions are prepared by incorporating the active component in the required amount of solvent agent, together with other desirable agents as enumerated above, followed by sterilization, generally by micro-membrane filtration.

Generally, dispersions are prepared by incorporating the various sterilized ingredients into a sterile dispersing medium containing the other required ingredients from among those enumerated above.

Sterile powders for the contemporaneous preparation of injectable solutions are geenerally prepared by vacuum or freeze-drying of previously sterilized solutions of the active component and any additional agents.

In parenteral preparations, the compositions contain from about 0.1 to about 500 mg/ml of the active components, with about 0.5 to about 250 mg/ml being preferred. Daily parenteral dosages are determined for the particular host, but range between about 0.1 mg/kg to about 10 mg/kg.

In order to enable one skilled in the art to practice the present invention, the following preparative examples of compounds in accordance with the present invention are provided. These examples, however, are merely illustrative and are not to be read as limited the scope of the invention as it is defined by the appended claims.

EXAMPLE 1

4-Amino-3-fluoro-1-(2,3,5-tri-O-benzoyl-β-D-ribofuranosyl)-2(1H)-pyridinone

A.

4-Amino-2,3,5,6-tetrafluoropyridine

A mixture of 20.0 g (118 mmol) of pentafluoropyridine (Aldrich Chemical Company, Milwaukee, Wis., USA) and 40 ml of concentrated aqueous ammonia was heated on a steam bath for two hours in a sealed stainles steel reaction vessel. The vessel and contents were cooled to room temperature and the resulting suspension suspension was partitioned between water and diethyl ether.

The water layer was extracted with ether and the ether solutions were combined and dried over anhydrous magnesium sulfate. Evaporation of the ether yielded 16.3 g (83.0%) of the title compound as a white solid of sufficient purity for use in the next reaction step.

The material exhibited an $R_f$ value of 0.4 when chromatographed on a thin-layer silica gel plate using chloroform as the eluant. A minor impurity ($R_f=0.2$) was also observed.

Recrystallization of the reaction product from cyclohexane provided pure material, mp 80°-82° C. (sublimation).

B.

4-Amino-3,5,6-trifluoro-2(1H)-pyridinone

A suspension of 18.7 g (113 mmol) of 4-amino-2,3,5,6-tetrafluoropyridine in 500 ml of 1M aqueous sodium hydroxide solution was heated under reflux for five hours. During the course of the reaction, some of the starting material sublimed into the condensor, and was cautiously washed back into the reaction mixture with small amounts of diethyl ether.

At the end of five hours, the reaction mixture was cooled and neutralized with concentrated hydrochloric acid. The white solid which precipitated was collected by filtration, dissolved in methanol, and filtered to remove undissolved solids. The methanol solution was evaporated, and the residue was redissolved in ethyl acetate and filtered to remove undissolved solids. The ethyl acetate solution was evaporarted to yield 7.14 g of crude product.

The aqueous filtrate from the original reaction mixture was extracted with several portions of ethyl acetate, with addition of conentrated hydrochloric acid as needed to maintain neutral pH. When an emulsion developed, acetic acid was added to acidify the mixture. The combined ethyl acetate extracts were combined, dried over anhydrous magnesium sulfate, and evaporated to yield an additional 10.68 g of crude reaction product. The overall yield of crude title compound was 18.08 g (97.9%). The material was of sufficient purity for use in the next reaction step.

The material exhibited an $R_f$ value of 0.4 when chromatographed on a thin-layer silica gel plate using 50:1 dichloromethane-methanol as the eluant.

Recrystallization of the reaction product from toluene provided pure 4-amino-3,5,6-trifluoro-2(1H)-pyridinone, mp 199°–201° C.

C.

4-Amino-3-fluoro-2(1H)-pyridinone and 4-amino-5-fluoro-2(1H)-pyridinone

A mixture of 18.42 g (112 mmol) of the 4-amino-3,5,6-trifluoro-2(1H)-pyridinone in 500 ml of ethanol and 106.5 ml (336 mmol) of anhydrous hydrazine was heated under reflux overnight. At the end of this period, thin-layer chromatographic analysis (silica gel, 10:1 acetonitrile-water eluant) of the reaction mixture indicated no starting material, but rather, the presence of a major product ($R_f$=0.4) and a minor product ($R_f$=0.3).

The reaction mixture was filtered to remove undissolved solids, and the filtrate was evaporated to give a residue which was coevaporated with ethanol several times. The final residue was dissolved in methanol and filtered to remove undissolved solids. To the filtrate were added 100 g of silica gel to produce a powder. The powder was added to a column of 650 g of silica gel which had been packed using 20:1 acetonitrile-water. The column was then eluted with 20:1 acetonitrile-water to provide, first, 11.76 g (82.2%) of 4-amino-3-fluoro-2(1H)-pyridinone, mp 222°–226° C. as a light yellow solid, and next, 1.55 g (10.8%) of 4-amino-5-fluoro-2(1H)-pyridinone, mp 228°–236° C. Continued elution provided an additional 0.71 g of contaminated 4-amino-5-fluoro-2(1H)-pyridinone.

D.

4-Amino-3-fluoro-1-(2,3,5-tri-O-benzoyl-β-D-ribofuranosyl)-2(1H)-pyridinone

A sample of 9.70 g (75.8 mmol) of 4-amino-3-fluoro-2(1H)-pyridinone was dried under vacuum at 90° C. overnight. The dried material was dissolved in 500 ml of hexamethyldisilazane (Aldrich Chemical Co., Milwaukee, Wis., USA), and 100 mg of ammonium sulfate was added. The mixture was heated under reflux for 24 hours, protecting the reaction mixture from moisture. The resulting brown solution was evaporated on a rotary evaporator to yield a brown viscous oil. To this residue were added 500 ml of previously dried 1,2-dichloroethane and 42.01 g (83.3 mmol) of previously dried 1-O-acetyl-2,3,5-tri-O-benzoyl-β-D-ribofuranose (Petrarch Systems, Inc. 2731 Bartram Ave., Bristol, PA 19007, USA). The solution was cooled in an ice-bath and 90.8 mmol of stannic chloride was added in one portion. The resulting solution was stirred in an ice-bath for 15 minutes, and then at room temperature overnight while being protected from moisture all the while.

The resulting solution was poured into an ice-cold saturated solution of sodium bicarbonate, stirred, and filtered through Celite ® filter aid. The filter cake was washed well with dichloromethane and the aqueous and organic phases of the filtrate were separated. The aqueous phase was extracted with dichloromethane, and the organic solutions combined and dried over anhydrous magnesium sulfate. The dried solution was evaporated to yield 48.5 g of a foamy yellow solid. This material was dissolved in a minimum volume of dichloromethane and the resulting solution was charged to a silica gel column which had been previously packed under dichloromethane. Elution with 100:1 dichloromethane-methanol yielded, first, 11.86 g (27.4%) of slightly contaminated 4-amino-3-fluoro-1-(2,3,5-tri-O-benzoyl-β-D-ribofuranosyl)-2(1H)-pyridinone, followed by 26.56 g (61.3%) of pure product.

The material exhibited an $R_f$ value of 0.4 when chromatographed on a thin-layer silica gel plate using 20:1 dichloromethane-methanol as the eluant.

EXAMPLE 2

4-Amino-3-fluoro-1-(β-D-ribofuranosyl)-2(1H)-pyridinone

A solution of 26.56 g (46.4 mmol) of 4-amino-3-fluoro-1-(2,3,5-tri-O-benzoyl-β-D-ribofuranosyl)-2(1H)-pyridinone in 510 ml of 0.1M sodium methoxide in methanol (51.0 mmole, prepared from methanol and sodium spheres), was stirred for 24 hours at room temperature. At the end of this period, thin-layer chromatographic analysis of the reaction mixture (silica gel plate, 4:1 dichloromethane-methanol) indicated complete conversion to the product, $R_f$=0.3.

Approximately 100 ml of methanol-washed IRC-50 ion exchange resin (Dow Chemical Co., Midland, Mich., USA) in the hydrogen ion form was added to the solution, and stirring was continued for an additional two hours. At the end of this period, the mixture tested neutral with indicator paper, and the resin was removed by filtration, washed with methanol, and discarded. The methanol washings were combined with the filtrate, and the mixture was coevaporated with ethanol several times. The gummy residue was triturated with diethyl ether to remove the methyl benzoate to yield a white solid residue. Recrystallization from ethanol produced 8.33 g (69.0%) of 4-amino-3-fluoro-1-(β-D-ribofuranosyl)-2(1H)-pyridinone, mp 234°–236° C.

EXAMPLE 3

4-Amino-3-fluoro-1-(5-O-phosphono-β-D-ribofuranosyl)-2(1H)-pyridinone, disodium salt and 4-amino-3-fluoro-1-(5-O-phosphono-β-D-ribofuranosyl)-2(1H)-pyridinone, free acid To an ice-coled solution of 2.6 g (10 mmol) of 4-amino-3-fluoro-1-(β-D-ribofuranosyl)-2(1H)-pyridinone in 60 ml of trimethylphosphate were added dropwise 1.53 g (10 mmol) of phosphoryl chloride over a period of ten minutes. The solution was stirred at 5° C. for three hours after which time 382 mg (2.5 mmol) of phosphoryl chloride were added.

The resulting mixture was stirred for an additional hour and then poured into 100 g of ice water containing 8 g (95 mmol) of sodium bicarbonate. This solution was stirred for one hour at room temperature and then extracted twice with diethyl ether.

The aqueous layer from this extraction was mixed with 10 g of silica gel and the resulting mixture was evaporated under vacuum. The residual solid was suspended in acetonitrile and charged to a chromatographic column containing 280 g of silica gel previously packed under 4:1 acetonitrile-water.

Elution of the column with 4:1 acetonitrile-water provided a pure, chloride free fraction which was filtered through Celite ® filter aid and evaporated to dryness under reduced pressure. The white residue was triturated with absolute ethanol and then dried under reduced pressure at 5° C. for 24 hours to yield 3.0 g (75%) of 4-amino-3-fluoro-1-(5-O-phosphono-β-D-ribofuranosyl)-2-(1H)-pyridinone, disodium salt.

The free acid form, 4-amino-3-fluoro-1-(5-O-phosphono-β-D-ribofuranosyl)-2(1H)-pyridinone, was obtained from the disodium salt by passage of an aqueous solution of the latter through a Dowex-50 (Dow Chemical Co., Midland, Mich., USA) ion exchange column in the hydrogen ion form.

EXAMPLE 4

4-Amino-3-fluoro-1-(2,3,5-tri-O-acetyl-β-D-ribofuranosyl)-2(1H)-pyridinone

A mixture of 2.6 g (10 mmol) of 4-amino-3-fluoro-1-(β-D-ribofuranosyl)-2(1H)-pyridinone, 100 mg of N,N-dimethylaminopyridine, and 4.5 ml (45 mmol) of acetic anhydride was stirred at room temperature for 5 hours. The solvent was evaporated under vacuum and the residue was coevaporated twice with water.

The residue was triturated with water and collected by filtration. Recrystallization of the material from water-ethanol, provided 3.0 g of 4-amino-3-fluoro-1-(2,3,5-tri-O-acetyl-β-D-ribofuranosyl)-2(1H)-pyridinone.

EXAMPLE 5

4-Amino-1-[3,5-di-O-(4-methylbenzoyl)-β-D-erythropentofuranosyl]-3-fluoro-2(1H)-pyridinone and 4-amino-1-(2-deoxy-3,5-di-O-(4-methylbenzoyl)-α-D-erythro-pentofuranosyl]-3-fluoro-2(1H)-pyridinone A suspension of 50 mmol of 4-amino-3-fluoro-2(1H)-pyridinone in 250 ml of hexamethyldisilazane was heated under reflux overnight with a small amount of ammonium sulfate. The resulting solution was cooled and the excess hexamethyldisilazane was evaporated under reduced pressure. To the liquid residue were added 250 ml of dry 1,2-dichloroethane.

To the resulting solution were added 19.44 g (50 mmol) of 2-deoxy-3,5-di-O-(4-methylbenzoyl)-D-erythropentofuranosyl chloride, followed by 250 ml of dry 1,2-dichloroethane. The resulting solution was cooled to −25° C. in a dry ice-isopropanol mixture, and to the resulting suspension were added over a period of 30 minutes, a solution of 2.4 ml (125 mmol) of trimethylsilyl trifluoromethylmethanesulfonate in 100 ml of dry 1,2-dichloroethane. The addition was made slowly in order to maintain the reaction mixture temperature below −25° C.

The mixture was allowed to warm to room temperature, and was stirred overnight. The resulting mixture was poured into an ice-cold aqueous solution of sodium bicarbonate and the resulting mixture was diluted with 1,2-dichloromethane. The organic layer was separated and the aqueous layer was extracted with dichloromethane. The organic layers were combined, washed with saturated aqueous sodium chloride solution, and dried over anhydrous magnesium sulfate.

The solvents were evaporated under reduced pressure to yield 24.0 g of a foamy yellow solid which thin-layer chromatographic analysis (silica gel plate, eluted with 2:1 dichloromethane-ethyl acetate) showed to consist of two products, $R_f = 0.25$ and $R_f = 0.3$ which were presumed to be the α and β epimers.

The mixture was dissolved in dichloromethane and charged to a column of 1 kg of silica gel (230–240 mesh) packed under dichloromethane. Elution of the column, initially with 10:1 dichloromethane-ethyl acetate and gradually changing to 2:1 dichloromethane-ethyl acetate, gave three fractions. The first fraction was evaporated to yield 5.10 g (21.3%) of a white solid which was later confirmed to be 4-amino-1-[3,5-di-O-(4-methylbenzoyl)-β-D-erythro-pentofuranosyl]-3-fluoro-2(1H)-pyridinone.

The second fraction was evaporated to yield 9.66 g (40.3%) of a mixture of the two epimers, and the third fraction was evaporated to yield 5.10 g (21.3%) of a white solid which was later confirmed to be 4-amino-1-[3,5-di-O-(4-methylbenzoyl)-α-D-erythro-pentofuranosyl]-3-fluoro-2(1H)-pyridinone.

EXAMPLE 6

4-Amino-1-(2-deoxy-β-D-erythro-pentofuranosyl)-3-fluoro-2(1H)-pyridinone

A solution of 5.8 g (12 mmol) of 4-amino-1-[2-deoxy-3,5-di-O-(4-methylbenzoyl)-β-D-erythro-pentofuranosyl]-3-fluoro-2(1H)-pyridinone in 133 ml (13 mmol) of a 0.1M solution of sodium methoxide in methanol was stirred at room temperature overnight. Methanol-washed IRC-50 ion exchange resin (hydrogen ion form) was added and the mixture was stirred until neutral to pH indicator paper.

The resin was removed by filtration, washed with methanol, and discarded. The filtrate and washings were combined, and the solution was evaporated under reduced pressure to yield a semi-solid residue. Trituration of the residue with diethyl ether yielded 1.4 g of an off-white solid. Two recrystallizations of this material from ethanol yielded 920 mg (31%) of 4-amino-1-(2-deoxy-β-D-erythro-pentofuranosyl)-3-fluoro-2(1H)-pyridinone which, after drying at 80° C. under reduced pressure over $P_2O_5$, melted at 168°–170° C.

EXAMPLE 7

4-Amino-1-(2-deoxy-α-D-erythro-pentofuranosyl)-3-fluoro-2(1H)-pyridinone

Employing the procedure of Example 6, 5.08 g (11 mmol) of 4-amino-1-[2-deoxy-3,5-di-O-(4-methylbenzoyl)-α-D-erythro-pentofuranosyl]-3-fluoro-2(1H)-pyridinone were converted to 4-amino-1-(2-deoxy-α-D-erythro-pentofuranosyl)-3-fluoro-2(1H)-pyridinone, mp 161°–163° C.

EXAMPLE 8

4-Amino-1-(2-deoxy-5-phosphono-β-D-erythro-pentofuranosyl)3-fluoro-2(1H)-pyridinone, disodium salt and
4-amino-1-(2-deoxy-5-phosphono-β-D-erythro-pentofuranosyl)-3-fluoro-2(1H)-pyridinone, free acid 4-Amino-1-(2-deoxy-5-phosphono-β-D-erythro-pentofuranosyl)-3-fluoro-2(1H)-pyridinone, disodium salt and the corresponding free acid form, 4-amino-1-(2-deoxy-5-phosphono-β-D-erythro-pento-furanosyl)-3-fluoro-2(1H)-pyridinone, were prepared employing the procedure detailed above in Example 3.

EXAMPLE 9

4-Amino-1-(2-deoxy-3,5-di-O-acetyl-β-D-erythro-pentofuranosyl)-3-fluoro-2(1H)-pyridinone 4-Amino-1-(2-deoxy-3,5-di-O-acetyl-β-D-erythro-pentofuranosyl)-3-fluoro-2(1H)-pyridinone was prepared employing the procedure detailed in Example 4 above, but employing 4-amino-1-(2-deoxy-β-D-erythro-pentofuranosyl)-3-fluoro-2(1H)-pyridinone as the starting material.

EXAMPLE 10

4-Amino-3-bromo-2(1H)-pyridinone

To a solution of 0.25 g (2.3 mmol) of 4-aminopyridine (Aldrich Chemical Co., Milwaukee, Wis., USA) in 5 ml of acetic acid were added 0.44 g (2.5 mmol) of N-bromosuccinimide. The solution was stirred for two hours and then concentrated under vacuum, co-evaporating with ethanol.

The residual material was dissolved in methanol and 5 g of silica gel were added. The methanol was removed under vacuum, and the residual power was charged to a 100 g column of silica gel which had been packed under dichloromethane.

Elution of the column with 10:1 dichloromethane-methanol yielded 0.30 g (70%) of 4-amino-3-bromo-2(1H)-pyridinone, mp 255°–258° C.

EXAMPLE 11

4-Amino-3-bromo-1-(2,3,5-tri-O-benzoyl-β-D-ribofuranosyl)-2(1H)-pyridinone

A suspension of 1.9 g (10 mmol) of 4-amino-3-bromo-2(1H)-pyridinone and 100 mg of ammonium sulfate in 75 ml of hexamethyldisilazane was heated under reflux for 24 hours while being protected from moisture. The resulting solution was concentrated under vacuum to yield a bright yellow oil.

The oil was dissolved in 100 ml of previously dried 1.2-dichloroethane and to the resulting solution were added 5.07 g (10 mmol) of 1-O-acetyl-2,3,5-tri-O-benzoyl-β-D-ribofuranose and 50 ml of dry 1,2-dichloroethane. To this mixture were added 14.4 mmol of stannic chloride. The solution was stirred at room temperature for 24 hours and then poured into an ice-cold saturated aqueous solution of sodium bicarbonate.

The resulting emulsion was filtered through Celite ® filter aid and the organic and aqueous layers of the filtrate separated. The aqueous phase was extracted with dichloromethane, the organic phases combined, dried over anhydrous magnesium sulfate, and evaporated to yield 5.65 g (89.3%) of crude product as a foamy yellow solid.

This material was dissolved in dichloromethane and chromatographed on a 280 g column of silica gel, previously packed under 10:1 dichloromethane-ethyl acetate. Elution of the column with 10:1 dichloromethane-ethyl acetate yielded 3.52 g (55.6%) of 4-amino-3-bromo-1-(2,3,5-tri-O-benzoyl-β-D-ribofuranosyl)-2(1H)-pyridinone as an off-white foamy solid.

EXAMPLE 12

4-Amino-3-bromo-1-(β-D-ribofuranosyl)-2(1H)-pyridinone

A solution of 3.52 g (5.6 mmol) of 4-amino-3-bromo-1-(2,3,5-tri-O-benzoyl-β-D-ribofuranosyl)-2(1H)-pyridinone and 0.556 mmol of sodium methoxide in 50 ml of methanol was stirred at room temperature for 24 hours. At the end of this time, 0.88 g of methanol-washed IRC-50 ion exchange resin (Dow Chemical Co., Midland, Mich., USA) in the hydrogen ion form were added to the solution, and the resulting mixture was stirred for one hour.

At the end of one hour, the mixture tested neutral to pH indicator paper, and the resin was removed by filtration, washed with methanol, and discarded. The methanol filtrate and washings were combined and concentrated by coevaporation with toluene under vacuum.

The residue was triturated with diethyl ether and then recrystallized from ethanol to give 0.71 g (40%) of the title compound as a white solid, mp 202°–204° C.

EXAMPLE 13

4-Amino-3-chloro-2(1H)-pyridinone

To a solution of 0.25 g (2.3 mmol) of 4-amino-2(1H)-pyridinone in 5 ml of acetic acid were added 0.33 g (2.5 mmol) of N-chlorosuccinimide. The resulting solution was stirred for 2 hours and then concentrated under vacuum, coevaporating with ethanol.

The residue was dissolved in methanol and 5 g of silica gel were added. The methanol was removed under vacuum, and the resulting powder charged to a 100 g column of silica gel previously packed under dichloromethane. Elution of the column with 10:1 dichloromethane-methanol yielded 0.22 g (67%) of 4-amino-3-chloro-2(1H)-pyridinone as an off-white solid, mp 264°–267° C.

EXAMPLE 14

4-Amino-3-chloro-1-(2,3,5-tri-O-benzoyl-β-D-ribo furanosyl)-2(1H)-pyridinone

A suspension of 2.13 g (14.7 mmol) of 4-amino-3-chloro-2(1H)-pyridinone and 100 mg of ammonium sulfate in 50 ml of hexamethyldisilazane was heated under reflux for 24 hours, protected from moisture. The resulting mixture was evaporated under vacuum to yield a gold-colored oil.

This oil was dissolved in 100 ml of 1,2-dichloroethane and to the resulting solution were added 7,43 g (14.7 mmol) of 1-O-acetyl-2,3,5-tri-O-benzoyl-β-D-ribofuranose and an additional 100 ml of 1,2-dichloroethane. This solution was cooled in an ice bath and 3,41 ml (17.6 mmol) of trimethylsilyl trifluoromethylmethanesulfonate were added. The resulting solution was stirred at room temperature for 24 while being protected from moisture, and then poured into an ice-cold saturated aqueous solution of sodium bicarbonate.

The organic and aqueous layers were separated, and the aqueous layer was extracted with dichloromethane. The organic phases were combined, dried over anhydrous magnesium sulfate, and concentrated to yield 8.55 g (98.7%) of the crude title compound as a foamy yellow solid.

This material was dissolved in dichloromethane and charged to a 500 g column of silica gel, previously packed under 5:1 dichloromethane-ethyl acetate. Elution of the column with the same solvent system yielded 5.0 g (57.7%) of 4-amino-3-chloro-1-(2,3,5-tri-O-benzoyl-β-D-ribofuranosyl)-2(1H)-pyridinone as a foamy white solid.

EXAMPLE 15

4-Amino-3-chloro-1-(β-D-ribofuranosyl)-2(1H)-pyridinone

A solution of 5.0 g (8.5 mmol) of 4-amino-3-chloro-1-(tri-O-benzoyl-β-D-ribofuranosyl)-2(1H)-pyridinone and 8.5 mmol) of sodium methoxide in 85 ml of methanol was stirred for 24 hours at room temperature. At the end of this time, thin-layer chromatographic analysis (silica gel plate, eluted with 4:1 dichloromethane-methanol) showed the reaction to be incomplete, so the mixture was stirred for an additional 24 hours, followed by heating just to boiling.

The solution was cooled, and 5 g of methanol-washed IRC-50 resin (Dow Chemical Co., Midland, Mich., USA) in the hydrogen ion form were added and the mixture was stirred for one hour. After this time, the mixtures tested neutral with pH indicator paper, and the resin was removed by filtration, washed with methanol, and discarded.

The filtrate and washings were combined, and concentrated under vacuum, coevaporating with toluene. The residue was triturated with diethyl ether and recrystallized froim ethanol to give 1.70 g (72.3%) of 4-amino-3-chloro-1-(β-D-ribofuranosyl)-2(1H)-pyridinone as a white solid, mp 197°–199° C.

We claim:

1. A compound having the structural formula

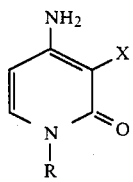

where R is selected from

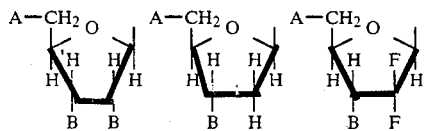

wherein X is fluorine, chlorine, or bromine, and A is hydrogen, $H_2PO_4$, benzoyl, 4-methylbenzoyl, acetyl, propionyl or straight or branched-chain alkanoyl of from four to six carbon atoms, and B is hydrogen, benzoyl, 4-methylbenzoyl, acetyl, propionyl or straight or branched-chain alkanoyl of from four to six carbon atoms, and the pharmaceutically acceptable salts thereof.

2. A compound as defined in claim 1 wherein X is fluorine.

3. A compound as defined in claim 2 which is 4-amino-3-fluoro-1-β-D-ribofuranosyl-2(1H)-pyridinone.

4. A compound as defined in claim 2 which is 4-amino-3-fluoro-1-(5-O-phosphono-β-D-ribofuranosyl)-2(1H)-pyridinone and the pharmaceutically acceptable base addition salts thereof.

5. A compound as defined in claim 4 which is 4-amino-3-fluoro-1-(5-O-phosphono-β-D-ribofuranosyl)-2(1H)-pyridinone, disodium salt.

6. A compound as defined in claim 2 which is 4-amino-3-fluoro-1-(2,3,5-tri-O-acetyl-β-D-ribofuranosyl)-2(1H)-pyridinone.

7. A compound as defined in claim 2 which is 4-amino-3-fluoro-1-(2,3,5-tri-O-benzoyl-β-D-ribofuranosyl)-2-(1H)-pyridinone.

8. A compound as defined in claim 2 which is 4-amino-1-(2-deoxy-β-D-erythro-pentofuranosyl)-3fluoro-2(1H)-pyridinone.

9. A compound as defined in claim 2 which is 4-amino-1-(2-deoxy-5-O-phosphono-β-D-erythro-pentofuranosyl)-3-fluoro-2(1H)-pyridinone and the pharmaceutically acceptable base addition salts thereof.

10. A compound as defined in claim 9 which is 4-amino-1-(2-deoxy-5-O-phosphono-β-D-erythro-pentofuranosyl)-3-fluoro-2(1H)-pyridinone, disodium salt.

11. A compound as defined in claim 2 which is 4-amino-1-(2-deoxy-3,5-di-O-acetyl-β-D-erythropentofuranosyl)-3-fluoro-2(1H)-pyridinone.

12. A compound as defined in claim 2 which is 4-amino-1-[2-deoxy-3,5-di-O-(4-methylbenzoyl)-β-D-erythro-pentofuranosyl]-3-fluoro-2(1H)-pyridinone.

13. A compound as defined in claim 1 wherein X is chlorine.

14. A compound as defined in claim 13 which is 4-amino-3-chloro-1-(2,3,5-tri-O-benzoyl-β-D-ribofuranosyl)-2(1H)-pyridinone.

15. A compound as defined in claim 13 which is 4-amino-3-chloro-1-(β-D-ribofuranosyl)-2(1H)pyridinone.

16. A compound as defined in claim 1 wherein X is bromine.

17. A compound as defined in claim 16 which is 4-amino-3-bromo-1-(2,3,5-tri-O-benzoyl-β-D-ribofuranosyl)-2(1H)-pyridinone.

18. A compound as defined in claim 16 which is 4-amino-3-bromo-1-(β-D-ribofuranosyl)-2(1H)-pyridinone.

19. A pharmaceutical composition comprising an antivirally effective amount of a compound in accordance with claim 1 in combination with a pharmaceutically acceptable carrier.

20. A method of treating viral infections in a mammal comprising administering to a mammal in need of such treatment an antivirally effective amount of a compound in accordance with claim 1 in combination with a pharmaceutically acceptable carrier.

* * * * *